US010563239B2

(12) United States Patent
van der Meulen et al.

(10) Patent No.: US 10,563,239 B2
(45) Date of Patent: Feb. 18, 2020

(54) PROCESS OF USING A PLUG FLOW HYDROLYSIS REACTOR HAVING A SLURRY INTRODUCTION DEVICE

(71) Applicant: Iogen Energy Corporation, Ottawa (CA)

(72) Inventors: Torbjorn van der Meulen, Ottawa (CA); Lee Castiglione, Ottawa (CA); Stephanie Lepine, Ottawa (CA)

(73) Assignee: Iogen Energy Corporation, Ottawa (CA)

( * ) Notice: Subject to any disclaimer, the term of this patent is extended or adjusted under 35 U.S.C. 154(b) by 0 days.

(21) Appl. No.: 15/538,850

(22) PCT Filed: Dec. 22, 2015

(86) PCT No.: PCT/CA2015/051362
§ 371 (c)(1),
(2) Date: Jun. 22, 2017

(87) PCT Pub. No.: WO2016/101073
PCT Pub. Date: Jun. 30, 2016

(65) Prior Publication Data
US 2017/0349923 A1 Dec. 7, 2017

Related U.S. Application Data

(60) Provisional application No. 62/095,931, filed on Dec. 23, 2014.

(30) Foreign Application Priority Data

Jan. 6, 2015 (CA) .................................... 2876672

(51) Int. Cl.
| C12P 19/14 | (2006.01) |
| C12P 7/14 | (2006.01) |
| C12M 1/00 | (2006.01) |
| C12M 1/06 | (2006.01) |
| C12P 19/02 | (2006.01) |
| C12M 1/40 | (2006.01) |

(52) U.S. Cl.
CPC ............ *C12P 19/14* (2013.01); *C12M 21/18* (2013.01); *C12M 27/02* (2013.01); *C12M 45/09* (2013.01); *C12P 7/14* (2013.01); *C12P 19/02* (2013.01); *C12Y 302/01004* (2013.01); *C12Y 302/01021* (2013.01)

(58) Field of Classification Search
None
See application file for complete search history.

(56) References Cited

U.S. PATENT DOCUMENTS

| 4,409,329 A | 10/1983 | Silver |
| 4,788,040 A | 11/1988 | Campagnolo et al. |
| 5,192,465 A | 3/1993 | Petrich et al. |
| 5,248,484 A | 9/1993 | Scott et al. |
| 5,258,293 A | 11/1993 | Lynd et al. |
| 5,261,485 A | 11/1993 | Thornton et al. |
| 5,354,460 A | 10/1994 | Kearney et al. |
| 5,411,594 A | 5/1995 | Brelsford |
| 5,733,758 A | 3/1998 | Nguyen |
| 5,837,506 A | 11/1998 | Lynd et al. |
| 5,888,806 A | 3/1999 | Nguyen |
| 7,001,521 B2 | 2/2006 | Paananen et al. |
| 7,598,069 B2 | 10/2009 | Felby et al. |
| 7,754,457 B2 | 7/2010 | Foody et al. |
| 8,623,175 B2 * | 1/2014 | Rolland .................... B30B 9/06 162/243 |
| 8,709,770 B2 | 4/2014 | Harlick et al. |
| 8,940,131 B2 | 1/2015 | Rolland |
| 9,169,505 B2 | 10/2015 | Rolland |
| 2006/0278578 A1 | 12/2006 | Dornfeld |
| 2009/0035826 A1 | 2/2009 | Tolan et al. |
| 2009/0053777 A1 | 2/2009 | Hennessey et al. |
| 2009/0098616 A1 | 4/2009 | Burke et al. |
| 2010/0190226 A1 | 7/2010 | Foody et al. |

(Continued)

FOREIGN PATENT DOCUMENTS

| CA | 2724169 A1 | 11/2009 |
| CA | 2808666 A1 | 3/2012 |

(Continued)

OTHER PUBLICATIONS

D.G. Peacock and J.F. Richardson, "Flow Characteristics of Reactors—Flow Modelling", Chemical Engineering vol. 3: Chemical and Biochemical Reactors . . . , vol. 3, pp. 79-83 (2012).
D.G. Rao, Introduction to Biochemical Engineering, pp. 217-226 (2010).
X. Shao et al., "Reactor scale up for biological conversion of cellulosic biomass to ethanol", Bioprocess Biosyst Eng 33, pp. 485-493 (2010).
B.H. Um, "Optimization of Ethanol Production from Concentrated Substrate", a Dissertation submitted to the Graduate Faculty of Auburn University in Partial Fulfillment of the Requirements for the Degree of Doctor of Philosophy, Auburn, Alabama, pp. 1-268, Aug. 4, 2007.
International Search Report and Written Opinion that was issued in PCT/CA2015/051362 filed Dec. 22, 2015.
J.M. Winterbottom and M. King, "Non-ideal flow in chemical reactors and the residence time distribution", Reactor Design for Chemical Engineers, pp. 252-254 (1999).

*Primary Examiner* — Christian L Fronda
(74) *Attorney, Agent, or Firm* — Venable LLP

(57) ABSTRACT

Provided herein is a process for hydrolyzing a cellulosic feedstock to produce sugar. The process comprises introducing a pretreated cellulosic slurry to an inlet region of a plug flow hydrolysis reactor using a slurry introduction device that reduces the axial momentum of the slurry at the surface of the reactor contents. The cellulosic feedstock slurry is hydrolyzed in the plug flow hydrolysis reactor by contacting the cellulosic feedstock with at least cellulase enzymes to produce glucose. Also provided herein is a vertically-oriented, unmixed downflow hydrolysis reactor for hydrolyzing a pretreated cellulosic feedstock slurry (Continued)

which comprises such a slurry introduction device disposed in a top region thereof.

13 Claims, 3 Drawing Sheets

(56) References Cited

U.S. PATENT DOCUMENTS

| | | |
|---|---|---|
| 2010/0221819 A1 | 9/2010 | Foody et al. |
| 2011/0008850 A1 | 1/2011 | Rolland |
| 2012/0052534 A1 | 3/2012 | Harlick et al. |
| 2012/0055466 A1 | 3/2012 | Cotti Comettini et al. |
| 2012/0168389 A1 | 7/2012 | Kochergin et al. |
| 2012/0237983 A1 | 9/2012 | Harlick |
| 2014/0106412 A1 | 4/2014 | Rolland |
| 2014/0127756 A1 * | 5/2014 | Bolz ............... C12P 19/14 435/99 |
| 2014/0242684 A1 | 8/2014 | Harlick et al. |

FOREIGN PATENT DOCUMENTS

| | | |
|---|---|---|
| WO | 2005/118828 A1 | 12/2005 |
| WO | 2006/063467 A1 | 6/2006 |
| WO | 2009/045651 A2 | 4/2009 |
| WO | 2010/022511 A1 | 3/2010 |
| WO | 2010/113130 A2 | 10/2010 |
| WO | 2014/066145 A1 | 5/2014 |
| WO | 2014/160262 A1 | 10/2014 |

* cited by examiner

PROCESS OF USING A PLUG FLOW HYDROLYSIS REACTOR HAVING A SLURRY INTRODUCTION DEVICE

This application is a national stage application of PCT/CA2015/051362 having an international filing date of Dec. 22, 2015, which claims the benefit of U.S. Provisional Application No. 62/095,931 filed Dec. 23, 2014 and CA 2,876,672 filed Jan. 6, 2015, each of which is incorporated by reference herein.

TECHNICAL FIELD

The present invention provides a process for producing fermentable sugar from a cellulosic feedstock.

BACKGROUND

Much attention and effort has been applied in recent years to the production of fuels and chemicals, primarily ethanol, from cellulosic feedstocks, such as dedicated crops, agricultural residues and forestry residues, due to their low cost and wide availability. Dedicated crops such as switch grass do not currently have large markets. Since agricultural and forestry residues are typically burned and landfilled, using them for ethanol production offers an attractive alternative to disposal.

The production of ethanol or other fermentation products from cellulosic feedstock typically involves pretreatment of the feedstock to increase the cellulose surface area, with limited conversion of the cellulose to glucose. Pretreatment is followed by enzymatic hydrolysis of the cellulose remaining in the pretreated cellulosic feedstock with cellulase enzymes to produce glucose. Glucose is then converted to ethanol by microorganisms.

The cellulase enzymes utilized to hydrolyze the cellulose to glucose include a mix of enzymes including exo-cellobiohydrolases (CBH), endoglucanases (EG), beta-glucosidases and other enzymes. The CBH and EG enzymes catalyze the hydrolysis of the cellulose ($\beta$-1,4-D-glucan linkages). The CBH enzymes, CBHI and CBHII (also known as Cel7 and Cel6 according to Glycoside Hydrolase family designations), act on the ends of the glucose polymers in cellulose microfibrils and liberate cellobiose, while the EG enzymes (including EGI, EGII, EGIII and EGV, also known as Cel7, Cel5, Cel12 and Cel45, respectively) act at random locations on the cellulose. Together, the cellulase enzymes hydrolyze cellulose to cellobiose, which, in turn, is hydrolyzed to glucose by beta-glucosidase (beta-G). In addition to CBH, EG and beta-glucosidase, there are several accessory enzymes that aid in the enzymatic digestion of cellulose (see co-owned WO 2009/026722 (Scott), which is incorporated herein by reference, and Harris et al., 2010, Biochemistry, 49:3305-3316).

Enzymatic hydrolysis is typically conducted in one or more mixed batch reactors. However, in order for conventional stirred hydrolysis reactors to mix slurries effectively during the hydrolysis, a very large power input is often required. Furthermore, in a large commercial plant several batch hydrolysis reactors are required. These requirements can significantly increase the capital and operating costs of the hydrolysis process. Unmixed hydrolysis has the potential for cost savings by avoiding the equipment and power input associated with mixing.

Further, the inventors recognize that the use of a continuous unmixed hydrolysis with cellulase enzymes to produce glucose may offer the opportunity to decrease the cost of enzymatic hydrolysis. Continuous hydrolysis refers to slurry being fed into and withdrawn from a hydrolysis reactor continuously, as contrasted with batch hydrolysis in which the reactor is typically filled initially and emptied at the conclusion of hydrolysis. Carrying out hydrolysis in this manner offers a simpler operation and avoids the loss of efficiency during the filling and emptying of vessels associated with batch hydrolysis.

Despite the foregoing advantages associated with unmixed hydrolysis, problems can arise during operation. In an ideal continuous unmixed hydrolysis, slurries exhibit plug flow in which there is no or limited axial velocity gradient in the radial direction. However, the inventors have recognized that, during an actual continuous, unmixed hydrolysis, the slurries can channel. Channeling occurs when a portion of the slurry flows through the hydrolysis reactor more rapidly than expected from the reactor volume divided by the flow rate. In particular, channeling slurries exhibit axial velocity in the radial direction. Such phenomena might be a consequence of changes in the rheological properties of the slurry as the hydrolysis proceeds. In particular, as the hydrolysis proceeds, the slurry begins to flow more readily as the viscosity drops. This may lead to channel formation when significant changes in the axial velocity of the slurry are persistent in the radial direction.

Channeling can have several negative impacts on the hydrolysis of cellulose. Most notably, channeling reduces the residence time of the slurry in the reactor, which in turn reduces the cellulose conversion of the available reactor volume. Moreover, since some enzymes, such as $\beta$-glucosidase, do not bind to fiber solids, channel formation can reduce the residence time of this enzyme in the reactor. This can lead to significant reductions in glucose yield as $\beta$-glucosidase is necessary for converting cellobiose to glucose.

One problem that has been observed by the inventors during enzymatic hydrolysis is that when a feedstock slurry is introduced to the top region of an unmixed reactor, the momentum of the slurry stream which is introduced can create turbulence in the inlet region of the reactor contents. The inventors have discovered that this is particularly the case if an incoming stream or jet of material drops a significant distance into the slurry contents within the reactor. As discussed further herein, it has been found that such drop can create a region in the reactor contents in which plug flow is not maintained. Because of this effect, the result is a portion of the reactor contents channeling and another portion acting as a stagnant volume in the reactor. This reduces the volumetric efficiency of the reactor and results in lower cellulose conversion. Thus, there is a need in the art for continuous processes and reactor designs in which plug flow conditions are substantially maintained.

SUMMARY

In accordance with one embodiment of the invention, there is provided an improved process and reactor design for producing fermentable sugar from a cellulosic feedstock.

In certain embodiments, the process(es) described herein may provide benefits over known processes for converting cellulosic feedstock slurries to fermentable sugar by using cellulase enzymes. Disclosed herein are processes and reactor designs for hydrolyzing a pretreated cellulosic feedstock slurry employing a plug flow hydrolysis reactor comprising an inlet region having disposed therein a slurry introduction device that dissipates the momentum of the contents of the slurry in the inlet region of the plug flow hydrolysis reactor during or after the introduction of the slurry to the hydrolysis reactor. Reducing the slurry momentum can in turn promote a better distributed flow of the slurry during the hydrolysis and reduce stagnant volume in the reactor. A more even plug flow may improve the residence time of the slurry in the reactor, which in turn could enable an increase in the volumetric efficiency.

Thus, according to one aspect of the invention, there is provided a process for hydrolyzing a cellulosic feedstock, the process comprising the steps of: (i) providing a pretreated cellulosic feedstock slurry having an undissolved solids content of between about 5 wt % and about 40 wt % undissolved solids; (ii) conveying the pretreated cellulosic feedstock slurry to a plug flow hydrolysis reactor; (iii) introducing the cellulosic feedstock slurry to the plug flow hydrolysis reactor using a slurry introduction device that reduces axial momentum of the slurry at the surface of the reactor contents; and (iv) hydrolyzing the pretreated cellulosic feedstock slurry in the plug flow hydrolysis reactor by contacting the cellulosic feedstock with at least cellulase enzymes to produce glucose.

In some embodiments of the invention, the portion of the cellulose hydrolyzed in the unmixed reactor is between about 10 wt % and about 100 wt % or between about 10 wt % and about 70 wt %. According to another embodiment of the invention, a hydrolyzed cellulosic feedstock from step (iv) is fed to a mixed hydrolysis reactor and further hydrolyzed therein.

In further embodiments of the invention, the hydrolysis is carried out with beta-glucosidase.

The plug flow hydrolysis reactor or the mixed hydrolysis reactor, if such is utilized, may be one of a plurality of reactors in a system.

According to a second aspect of the invention, there is provided a process for producing a fermentation product from a cellulosic feedstock, the process comprising the steps of: (i) providing a pretreated cellulosic feedstock slurry having an undissolved solids content of between about 5 wt % and about 40 wt % undissolved solids; (ii) conveying the pretreated cellulosic feedstock slurry to a plug flow hydrolysis reactor; (iii) introducing the cellulosic feedstock slurry to the plug flow hydrolysis reactor using a slurry introduction device that reduces the axial momentum of the slurry at the surface of the reactor contents; (iv) hydrolyzing the pretreated cellulosic feedstock slurry in the plug flow hydrolysis reactor by contacting the cellulosic feedstock with at least cellulase enzymes to produce glucose; (v) optionally further hydrolyzing a partially hydrolyzed slurry produced in step (iv) in a mixed hydrolysis reactor; and (iv) fermenting glucose produced from step (iv) or (v) with microorganisms to produce the fermentation product. The fermentation product may be an alcohol, such as ethanol.

According to a third aspect of the invention, there is provided a system for hydrolyzing a cellulosic feedstock, the system comprising: (i) a pretreatment reactor for producing a pretreated cellulosic feedstock slurry; (ii) an apparatus for conveying the pretreated cellulosic feedstock slurry; and (iii) a plug flow hydrolysis reactor for receiving the pretreated cellulosic feedstock slurry from the apparatus and hydrolyzing the pretreated cellulosic feedstock therein with cellulase enzymes, the plug flow hydrolysis reactor comprising a slurry introduction device for reducing axial momentum at the surface of the reactor contents when the reactor is in operation.

In certain embodiments of the invention, the system further comprises a mixed hydrolysis reactor for receiving and hydrolyzing therein a feedstock slurry that has been partially hydrolyzed in the unmixed or plug flow hydrolysis reactor. The plug flow hydrolysis reactor may be a continuous reactor with a height-to-diameter ratio of about 0.2:1.0 to about 10.0:1.0.

According to a fourth aspect of the present invention, there is provided a vertically-oriented, unmixed downflow plug flow reactor for hydrolyzing a pretreated cellulosic feedstock slurry comprising: (i) a slurry introduction device for reducing axial momentum at the surface of the reactor contents when said reactor is in operation; and (ii) an outlet in a bottom region of the hydrolysis reactor for withdrawing slurry that is at least partially hydrolyzed from the reactor, the plug flow reactor having a height-to-diameter ratio of about 0.2:1.0 to about 10.0:1.0.

According to any of the foregoing aspects of the invention, the slurry introduction device is an inlet dissipator device. In one embodiment of the invention, the dissipator device comprises one or more distributor plates.

The present invention will be described with regard to further embodiments. However, it will be apparent to persons skilled in the art that a number of variations and modifications can be made without departing from the scope of the invention as defined in the claims.

DETAILED DESCRIPTION

Feedstock Processing Prior to Pretreatment

Figure 1A:
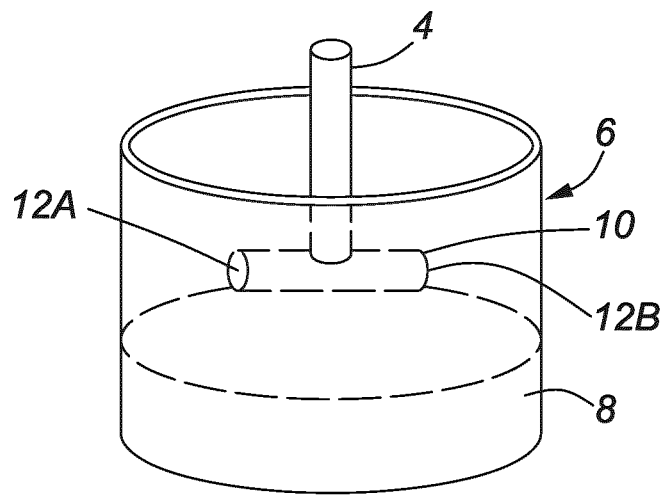
FIG. 1A is a slurry introduction device comprising vertical piping in an inlet region of a plug flow reactor with a rotating arm at its proximal end.

The feedstock for the process is a cellulosic material. By the term "cellulosic feedstock", it is meant any type of plant biomass such as, but not limited to, cultivated crops such as, but not limited to grasses, for example, but not limited to, C4 grasses, such as switch grass, cord grass, rye grass, *Miscanthus*, reed canary grass, or a combination thereof, sugar processing residues, for example, but not limited to, leaves and tops, and bagasse, such as sugar cane bagasse, beet pulp, or a combination thereof, agricultural residues, for example, but not limited to, soybean stover, corn stover, rice straw, sugar cane straw, rice hulls, barley straw, corn cobs, wheat straw, canola straw, oat straw, oat hulls, corn fiber, or a combination thereof, forestry biomass for example, but not limited to, recycled wood pulp fiber, sawdust, hardwood, for example aspen wood, softwood, or a combination thereof. Furthermore, the cellulosic feedstock may comprise cellulosic waste material or forestry residue materials such as, but not limited to, newsprint, cardboard and the like. Cellulosic feedstock may comprise one species of fiber or, alternatively, cellulosic feedstock may comprise a mixture of fibers that originate from different cellulosic feedstocks. In addition, the cellulosic feedstock may comprise fresh cellulosic feedstock, partially dried cellulosic feedstock, fully dried cellulosic feedstock, or a combination thereof. Moreover, new cellulosic feedstock varieties may be produced from any of those species listed above by plant breeding or by genetic engineering.

Cellulosic feedstocks comprise cellulose in an amount greater than about 20%, more preferably greater than about 30%, more preferably greater than about 40% (w/w). For example, the cellulosic material may comprise from about 20% to about 50% (w/w) cellulose, or any amount therebetween. Furthermore, the cellulosic feedstock comprises lignin in an amount greater than about 10%, more typically in an amount greater than about 15% (w/w). The cellulosic feedstock may also comprise small amounts of sucrose, fructose and starch.

Cellulosic feedstocks that have particle sizes of less than about 6 inches may not require size reduction. That is, such feedstocks may simply be slurried in water and then pumped to downstream stages of the process. For feedstocks of larger particle sizes, the cellulosic feedstock is generally subjected to size reduction by methods including, but not limited to, milling, grinding, agitation, shredding, compression/expansion, or other types of mechanical action. Size reduction by mechanical action can be performed by any type of equipment adapted for the purpose, for example, but not limited to, hammer mills, tub-grinders, roll presses, refiners and hydrapulpers. Preferably, at least 90% by volume of the particles produced from the size reduction may have a length less than between about 1/16 and about 6 in.

Before, during or subsequent to size reduction, the feedstock can be slurried in water, which allows the feedstock to be pumped. The desired weight ratio of water to dry cellulosic feedstock solids in the slurry is determined by factors such as pumpability, pipe-line requirements, and other practical considerations.

The solids concentration of the aqueous slurry of the cellulosic feedstock slurry is expressed as the undissolved solids (UDS) concentration. Prior to pretreatment, the cellulosic feedstock slurry UDS may be about 3% to about 30% or about 4% to about 20%. The weight ratio of dry solids to aqueous slurry is determined by the procedure set out in Example 1.

The feedstock fiber may be soaked with water or an aqueous solution comprising acid. Soaking may be carried out by introducing the cellulosic feedstock to a tank where it is mixed with hot water at relatively low solids consistency. Generally, the cellulosic feedstock will be subjected to size reduction prior to its introduction to the tank where soaking takes place. Moreover, the cellulosic feedstock may be leached as set forth in WO 02/070753 (Griffin, which is incorporated herein by reference).

After slurrying, leaching and/or soaking, the cellulosic feedstock may subsequently be dewatered by any suitable technique. For instance, dewatering may be carried out by utilizing devices that remove water under pressure from the aqueous feedstock slurry. Dewatering devices suitable for use in the invention includes pressurized screw presses or plug screw feeders, such as those described in WO 2010/022511 (incorporated herein by reference) and pressurized filters. The dewatering process optionally includes a pre-draining zone in order to drain out water from the feedstock slurry at atmospheric pressure or higher. This dewatered feedstock slurry is then sent to one or more devices for dewatering the slurry under pressure. Water expressed from the cellulosic feedstock by the dewatering step may be reused in the process.

Pretreatment of the Cellulosic Feedstock

The cellulosic feedstock is subjected to pretreatment prior to enzymatic hydrolysis to produce a pretreated cellulosic feedstock. The pretreatment is generally intended to deliver a sufficient combination of mechanical and chemical action so as to disrupt the fiber structure of the cellulosic feedstock and increase the surface area of the feedstock to make it accessible to cellulase enzymes. According to some embodiments, the pretreatment is performed so that a high degree of hydrolysis of the hemicellulose and only a small amount of conversion of cellulose to glucose occurs. The cellulose is hydrolyzed to glucose in a subsequent step that uses cellulase enzymes. In one embodiment, a dilute mineral acid, at a concentration from about 0.02% (w/w) to about 5% (w/w), or any amount therebetween, (measured as the percentage weight of pure acid in the total weight of dry feedstock plus aqueous solution) is used for the pretreatment.

The acid may be sulfuric acid, sulfurous acid, sulfur dioxide, hydrochloric acid or phosphoric acid. Preferably, the acid is sulfuric acid. The amount of acid added to the cellulosic feedstock may vary, but should be sufficient to achieve a final concentration of acid of about 0.02% to about 2% w/w, or any amount therebetween. The resulting pH of the feedstock is about pH 0.4 to about pH 3.5, or any pH range therebetween.

The acid pretreatment is preferably carried out at a maximum temperature of about 160° C. to about 280° C. However, in practice, there will be a time delay in the pretreatment process before the feedstock reaches this temperature range. The above temperatures correspond to those values reached after sufficient application of heat to reach a temperature within this range. The time that the feedstock is held within this temperature range may be about 6 seconds to about 3600 seconds, or about 15 seconds to about 750 seconds or about 30 seconds to about 240 seconds.

The pretreatment is typically carried out under pressure. For example, the pressure during pretreatment may be between about 50 and about 700 psig or between about 75 and about 600 psig, or any pressure range therebetween.

The feedstock may be heated with steam during or prior to pretreatment. Without being limiting, one method to carry this out is to use low pressure steam to partially heat the feedstock, which is then pumped to a heating train of several stages. Other means may be employed to heat the feedstock, such as commercially available mixing devices designed for introducing steam and optionally acid through spray nozzles.

One method of performing acid pretreatment of the feedstock is steam explosion using the process conditions set out in U.S. Pat. No. 4,461,648 (Foody, which is herein incorporated by reference). Another method of pretreating the feedstock slurry involves continuous pretreatment, meaning that the cellulosic feedstock is pumped through a reactor continuously. Continuous acid pretreatment is familiar to those skilled in the art; see, for example, U.S. Pat. No. 5,536,325 (Brink); WO 2006/128304 (Foody and Tolan); and U.S. Pat. No. 4,237,226 (Grethlein), which are each incorporated herein by reference. Additional techniques known in the art may be used as required such as the process disclosed in U.S. Pat. No. 4,556,430 (Converse et al.; which is incorporated herein by reference).

The acid pretreatment produces a composition comprising an acid pretreated feedstock. Sugars produced by the hydrolysis of hemicellulose during pretreatment are generally present in the composition and include xylose, glucose, arabinose, mannose, galactose or a combination thereof.

The aqueous phase of the pretreated feedstock composition may also contain the acid added during the pretreatment. When sulfuric acid is the acid utilized in the pretreatment, the composition comprising the pretreated feedstock additionally contains sulfate and/or bisulfate salts.

The composition comprising acid pretreated feedstock will also comprise acetic acid produced during acid pretreatment. The concentration of acetic acid in this stream may be between 0.1 and 20 g/L. Additional organic acids may be liberated during pretreatment, including galacturonic acid, formic acid, lactic acid and glucuronic acid. Pretreatment may also produce dissolved lignin and inhibitors such as furfural and hydroxymethyl furfural (HMF). Accordingly, the composition comprising acid pretreated feedstock may also contain these components.

According to one exemplary embodiment of the invention, the soluble components of the pretreated feedstock composition are separated from the solids. This separation may be carried out by washing the pretreated feedstock composition with an aqueous solution to produce a wash stream, and a solids stream comprising the unhydrolyzed, pretreated feedstock. Alternatively, the soluble component is separated from the solids by subjecting the pretreated feedstock composition to a solids-liquid separation using known methods such as centrifugation, microfiltration, plate and frame filtration, cross-flow filtration, pressure filtration, vacuum filtration and the like. Optionally, a washing step may be incorporated into the solids-liquids separation. The separated solids, which contain cellulose, may then be sent to enzymatic hydrolysis with cellulase enzymes in order to convert the cellulose to glucose. The enzymatic hydrolysis of cellulose using cellulase enzymes is described in more detail hereinafter.

The separated soluble component from the above-described separation, which includes the sugars released during pretreatment, the pretreatment acid and other soluble components, may then be fermented using a microorganism capable of fermenting the sugars derived from the hemicellulose component of the feedstock.

Pretreatment may also be carried out under alkaline conditions. Examples of suitable alkaline pretreatment processes include ammonia fiber expansion (AFEX) or dilute ammonia pretreatment. According to the AFEX process, the cellulosic biomass is contacted with ammonia or ammonium hydroxide, which is typically concentrated, in a pressure vessel. The contact is maintained for a sufficient time to enable the ammonia or ammonium hydroxide to swell (i.e., decrystallize) the cellulose fibers. The pressure is then rapidly reduced which allows the ammonia to flash or boil and explode the cellulose fiber structure. The flashed ammonia may then be recovered according to known processes. The AFEX process may be run at about 20° C. to about 150° C. or at about 20° C. to about 100° C. and all temperatures therebetween. The duration of this pretreatment may be about 1 minute to about 20 minutes, or any time therebetween.

Dilute ammonia pretreatment utilizes more dilute solutions of ammonia or ammonium hydroxide than AFEX. Such a pretreatment process may or may not produce any monosaccharides. Dilute ammonia pretreatment may be conducted at a temperature of about 100 to about 150° C. or any temperature therebetween. The duration for such a pretreatment may be about 1 minute to about 20 minutes, or any time therebetween.

Subsequent to pretreatment, the pretreated feedstock slurry is typically cooled prior to enzymatic hydrolysis to decrease it to a temperature at which the cellulase enzymes are active. It should be appreciated that cooling of the feedstock can occur in a number of stages utilizing flashing, heat exchange or other suitable means. In one embodiment of the invention, the pretreated feedstock is cooled to temperatures of about 100° C. and below before enzymatic hydrolysis.

Enzymatic Hydrolysis with a Plug Flow Reactor Comprising a Slurry Introducing Device that Promotes Plug Flow In general, the hydrolysis is continuous. The term "continuous" with reference to a hydrolysis refers to slurry being fed into and withdrawn from the hydrolysis reactor continuously. In batch hydrolysis a reactor is typically filled at the start of and emptied at the conclusion of each batch. Typically, with continuous flow-through hydrolysis, the reactor is filled to the desired level initially, and thereafter, the slurry feed to the top and the product withdrawal from the bottom are maintained at substantially steady and equal rates.

The hydrolysis reactor (also referred to herein as a "plug flow reactor" or an "unmixed reactor") is a continuous reactor suitable for conducting an enzymatic hydrolysis of a slurry with cellulase enzymes therein that does not cause any significant backmixing of its contents as is typically employed in mixed hydrolysis reactors. In conventional mixed hydrolysis reactors, mixing is provided by mechanical mixers such as top-mounted, side-mounted, or bottom-mounted agitators or eductors; rapid movement of liquid slurry streams pumped into or through the vessel; and/or introducing or generating gases or vapours in the vessel. Moreover, reactors are known that employ periodic mixing (also referred to herein as "intermittent mixing") as the slurry passes through mixing zones along the length of the reactor (see for example, U.S. Pat. No. 5,888,806 (Nguyen)).

Although the unmixed plug flow reactor may operate with a certain amount of localized mixing due to the introduction and withdrawal of liquid and solids from the system, such localized mixing does not result in any significant dispersal or blending of the reactor contents, as would occur in mixed reactors. For example, a small amount of localized mixing may occur at the bottom of an unmixed downflow reactor due to the action of a rotary bottom scraper or other devices employed for removing the reactor contents. The power required for the discharge of the slurry is typically less than 5%, 3% or 1% of the power required to fully mix the slurry using a mixed reactor of conventional hydrofoil impeller design.

The process comprises introducing the cellulosic feedstock to the plug flow hydrolysis reactor using a slurry introduction device that reduces the axial momentum of the slurry at the surface of the reactor contents. By "reduces", it is meant that the momentum of the slurry is reduced relative to introducing a slurry using a conventional inlet system having a single vertical downward feed pipe of diameter 0.1:1 of the reactor diameter, and a drop of at least 8 inches between the pipe outlet and the slurry surface. As used herein, the term "surface" of the reactor contents means 5% of the slurry volume at and below the top of the slurry contents.

The slurry introduction device may be an inlet dissipator device, which is any suitable internally disposed apparatus for decreasing the momentum of a pretreated cellulosic feedstock slurry as it is being introduced to the plug flow reactor so as to prevent or reduce channeling or other non-uniformity of slurry flow in an inlet region of the plug flow reactor. Without being bound by any particular theory, the inlet dissipator device is designed to disperse the slurry over the transverse cross-sectional area of the unmixed reactor or at an angle off-set from the direction of slurry flow.

According to various embodiments of the invention, the slurry introduction device in the plug flow reactor includes a radially extending member or inlet ports that serve to introduce the slurry to the reactor contents at the inlet region of the reactor radially over the transverse cross-sectional area thereof. Such an arrangement reduces channeling and promotes plug flow. It should be appreciated that the slurry need not be re-directed at 90 degrees from the direction of the incoming feed. That is, if the slurry is introduced via a central vertical pipe extending into the top of the reactor, the slurry may be gradually diverted outwardly into the reactor contents by the slurry introduction device. The slurry introduction device in the inlet region of the reactor can be of any suitable configuration known to those of skill in the art and may include devices with distributor plates, inverted cones, inlet ports that introduce the slurry radially, multiple feed inlets or inlet piping that extends into the reactor contents sufficiently to decrease the momentum of the slurry in the inlet region. The inlet dissipator device can be designed for a pressure drop to achieve improved flow distribution. In certain embodiments of the invention, the pressure drop in the inlet dissipator device is between 0.1 and 1 bar. The drop in pressure is determined by measuring the pressure at the outlet region of the device with and without the slurry introduction device and determining the difference in pressure.

In embodiments of the invention employing a downflow plug flow reactor, the inlet region of the reactor is the volume of the reactor measured from its top to a location that is 95% of the reactor height. The remaining volume of the reactor, excluding the outlet, typically does not comprise any mixing elements or other devices that impede slurry flow. The remaining volume, which excludes the outlet, may include the volume measured from a location that is 5% of the reactor height to 95% of the reactor height. The outlet may comprise a bottom mounted scraper or a cone for facilitating withdrawal of the slurry from the reactor.

Non-limiting examples of slurry introduction devices are described in FIGS. 1A-1D. FIG. 1A depicts an embodiment in which the slurry introduction device is an inlet dissipator device that comprises a vertical pipe 4 that terminates with a rotatable horizontal arm 10 having outlet ports 12A and 12B that extend over the slurry contents 8. In this embodiment, the diameter of the vertical pipe 4 is a ratio of 0.01:1 to 0.2:1 of the reactor diameter. The cellulosic feedstock slurry is introduced to the vertical piping 4 and flows downwardly through the vertical pipe 4 and into the rotating horizontal arm 10 and exits through outlet ports 12A and 12B. The horizontal arm 10 has a diameter of 0.01 to 0.2:1 of the reactor diameter and a length 0.05 to 0.6 of the reactor diameter. The rpm of the horizontal arm 10 can range from 0.5 to 5. By introducing the cellulosic slurry to the reactor contents through the feed tubes and rotating outlet ports 12A and 12B, the incoming slurry is distributed more evenly over the surface of the reactor contents 8.

Figure 1B:
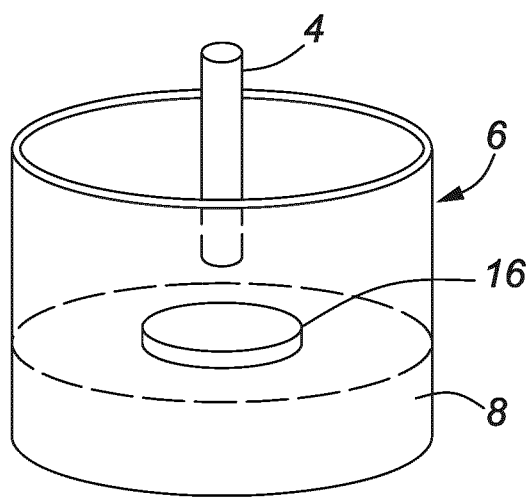
FIG. 1B is a slurry introduction device in an inlet region of a plug flow reactor comprising vertical piping with a distributor plate.

FIG. 1B depicts another embodiment in which the slurry introduction device is an inlet dissipator device that comprises vertical pipe 4 and a single distributor plate 16 positioned on the surface of the reactor contents 8. In this embodiment, the diameter of the vertical pipe 4 is 0.01:1 to 0.2:1 of the reactor diameter. The distributor plate 16 is in the shape of a disk, although other shapes can be employed such as a square or oval shape. The plate thickness is sufficient to handle the impact of the incoming feed and can be readily selected by a person of skill in the art. The diameter of the disk relative to that of the plug flow reactor diameter is 0.05 to 0.6. The disk 16 is supported by rods extending from the side walls of the reactor or from a top wall of the reactor (not shown). The disk 16 is positioned on top of the slurry, partly submerged or fully submerged within the top 5% of the slurry volume. The cellulosic slurry is introduced to the vertical pipe 4 and flows downwardly through the pipe 4. The slurry exits the outlet of the pipe 4, drops onto the disk-shaped distributor plate 16 and then flows over the plate. By flowing over the distributor plate 16, the momentum of the slurry is reduced, which in turn promotes more ideal plug flow of reactor contents 8.

In those embodiments in which vertical feed pipe 4 is employed, the incoming slurry may drop from the outlet of the piping to the surface of a radially extending member, such as a dispersion plate, by 4 inches to 90 inches, 5 inches to 70 inches, 6 inches to 60 inches, 7 inches to 50 inches or 8 inches to 40 inches, or any value therebetween.

Figure 1C:
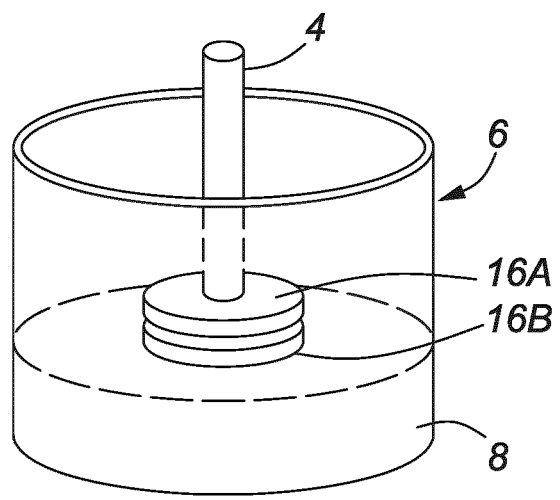
FIG. 1C is a slurry introduction device in an inlet region of a plug flow reactor comprising a vertical feed tube with a pair of distributor plates.

FIG. 1C depicts a similar embodiment in which the inlet dissipator device comprises vertical pipe 4 and two disk-shaped distributor plates, 16A and 16B positioned one on top of the other with a gap between them. In this embodiment, the vertical pipe 4 is connected to the top distributor plate 16A. The cellulosic feedstock slurry is fed through pipe 4 and flows through the gap between the distributor plates 16A and 16B. Passage of the slurry between the plates 16A and 16B creates a pressure drop that facilitates even distribution of the feed over the cross-sectional area of the distributor plates 16A and 16B. The diameter of the pipe 4 and distributor plates 16A and 16B is the same as that described above in relation to FIG. 1B. The position of the distributor plates 16A and 16B in relation to the slurry is similarly as described in FIG. 1B. As in FIG. 1B, the plates 16A and 16B can be attached via rods to the wall of the reactor or the top of the reactor. The distance between the plates is ¼ in. to 5 in.

Figure 1D:
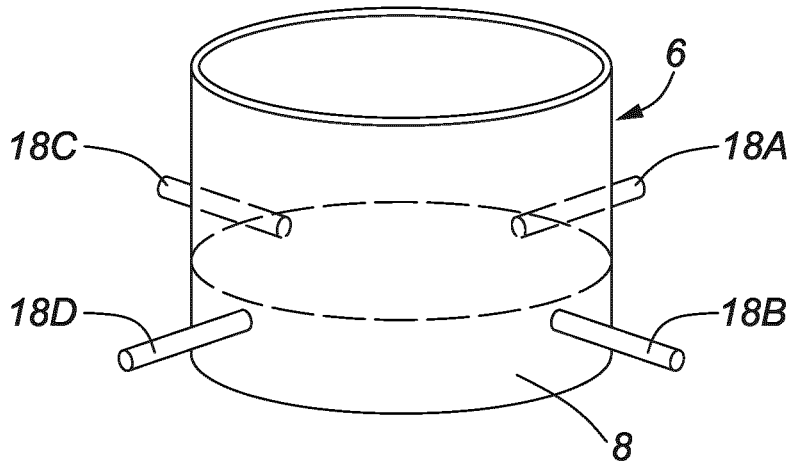
FIG. 1D is a slurry introduction device disposed in a plug flow reactor comprising multiple opposing feed ports configured to introduce slurry to the surface of the slurry contents horizontally through the wall of the reactor.

FIG. 1D describes a further embodiment in which the slurry introduction device comprises four opposing horizontal feed pipes 18A, 18B, 18C and 18D for introducing slurry in a radial direction through the wall of the plug flow reactor into the inlet region of the reactor 6. Similar to FIGS. 1A-C, the diameter of the horizontal feed pipes are 0.01:1 to 0.2:1 of the reactor diameter. The feed ports 18A, 18B, 18C and 18D are located at a height along the reactor such that the cellulosic feedstock slurry is introduced via the feed ports along the surface of the reactor contents 6. The horizontal feed pipes 18A, 18B, 18C and 18D can be positioned on top of the slurry, partly submerged or fully submerged within the top 5% of the slurry volume. Although four horizontal feed pipes are shown in FIG. 1D, 1 to 8 feed pipes can be employed or 2 to 8 feed pipes. By introducing the slurry with such a slurry introduction device, the momentum of the incoming slurry is reduced, which in turn promotes more ideal plug flow of reactor contents 8.

Other slurry introduction devices that can be used in the practice of embodiments of the invention include inverted cones and extended inlet piping. Similar to a distributor plate, an inverted cone reduces the momentum of the incoming cellulosic feedstock slurry by virtue of its flow over the surface of the cone. The diameter of the inverted cone relative to that of the plug flow reactor diameter is 0.05:1 to 0.6:1. An extended inlet pipe extends into, slightly above or on the top of the slurry contents so as to reduce slurry momentum and improve plug flow. The extended inlet pipe can extend into the reactor inlet region within a range of about 5 inches above or below the top of the slurry. The diameter of the extended inlet pipe relative to that of the plug flow reactor diameter may be 0.01:1 to 0.2:1.

As described previously, the reactor is designed so as to achieve a plug flow of reactor contents. By the phrase "substantially maintain a plug flow of reactor contents", it is meant that the reactor contents can flow through the reactor without any significant impediment to the slurry flow after flowing over or through the inlet dissipator device. For example, this excludes reactors having rotor and stator elements and that are designed to impart shear to the slurry and provide continual exposure of cellulose surface. Maintaining a plug flow or substantial plug flow of reactor contents is difficult to achieve in such reactors. Without being limiting, the unmixed reactor is typically cylindrical in transverse cross-section (taken perpendicular to the direction of slurry flow when the reactor is in use).

The average slurry residence time of the plug flow reactor may be at least 90% of the mean residence time (volume/flow rate).

By the term "vertically-oriented reactor", it is meant a reactor that is vertical or substantially vertical. By the term "substantially vertical", it is meant a reactor that, when in operation, is oriented up to 45° from a line drawn perpendicular to the surface on which the reactor is supported. In some embodiments of the invention, the reactor is oriented up to 30° from a line drawn perpendicular to horizontal.

The pretreated cellulosic feedstock slurry introduced to the unmixed hydrolysis reactor has between about 8 wt % and about 40 wt %, between about 10 wt % and about 40 wt %, or between about 12 wt % and about 40 wt % undissolved solids (UDS) or any range therebetween. In another embodiment of the invention, the pretreated cellulosic feedstock slurry has between about 15 wt % and about 30 wt % UDS, or any range therebetween or between about 15 wt % and about 24 wt % UDS (w/w). The undissolved solids content is based on dry weight of the solids and is measured according to the procedure set forth in Example 1.

The foregoing solids consistency range may be attained by dewatering various feedstock preparations prior to pretreatment including, for example, a soaked feedstock, a leached feedstock or any other feedstock slurry. Alternatively, a dewatering step can be conducted after pretreatment on the pretreated feedstock slurry. Without being limiting, suitable dewatering devices include screw presses, filters, centrifuges and extruders. In a further embodiment, the slurry may be prepared by the addition of sufficient amounts of water or aqueous solution to a feedstock that has been subjected to particle size reduction to attain a solids content in this range (see for example, WO 2009/125292 that is incorporated herein by reference).

The unmixed hydrolysis itself is a continuous operation. Typically, a continuous operation commences after a transient start-up as would be familiar to those of skill in the art. A suitable height-to-diameter ratio of an unmixed continuous hydrolysis reactor is between about 0.2:1.0 and about 10.0:1.0, between about 1:1 and about 6:1, between about 2:1 and about 6:1, or any ratio therebetween. The foregoing height-to-diameter ratios may represent the volume within the reactor occupied by the slurry itself rather than the dimensions of the reactor. It should be understood that, during operation, the unmixed hydrolysis reactor need not be full.

An example of a range for the diameter of the unmixed hydrolysis reactor is between about 1 ft and about 30 ft or between about 1 ft and about 25 ft.

The number of unmixed hydrolysis reactors in the system depends on the cost of the reactors, the volume of the aqueous slurry, and other factors. For a commercial-scale plant, the typical number of unmixed hydrolysis reactors may be, for example, 1 to 10. The unmixed reactors can be in a consecutive or parallel configuration. Those of ordinary skill in the art could readily select a suitable option by weighing the advantages and disadvantages of each design scheme.

The enzymatic hydrolysis of the cellulose to soluble sugars can be carried out with any type of cellulase enzymes suitable for such purpose, regardless of their source. Among the most widely studied, characterized and commercially produced cellulases are those obtained from fungi of the genera *Aspergillus, Humicola, Chrysosporium, Melanocarpus, Myceliopthora, Sporotrichum* and *Trichoderma*, and from the bacteria of the genera *Bacillus* and *Thermobifida*. The cellulase enzymes may comprise at least two cellobiohydrolase enzymes termed CBHI and CBHII (also known as Cel7 and Cel6 according to Glycoside Hydrolase family designations) and at least four EG enzymes including, but not limited to, EGI, EGII, EGIII and EGV (also known as Cel7, Cel5, Cel12 and Cel45, respectively). See Lynd et al., 2002, Microbiology and Molecular Biology Reviews, 66(3): 506-577 for a review of cellulase enzyme systems and Coutinho and Henrissat, 1999, "Carbohydrate-active enzymes: an integrated database approach." In Recent Advances in Carbohydrate Bioengineering, Gilbert, Davies, Henrissat and Svensson eds., The Royal Society of Chemistry, Cambridge, pp. 3-12).

The conversion of cellobiose to glucose is carried out by the enzyme β-glucosidase. By the term "β-glucosidase", it is meant any enzyme that hydrolyzes the glucose dimer, cellobiose, to glucose. The activity of the β-glucosidase enzyme is defined by its activity by the Enzyme Commission as EC#3.2.1.21. The β-glucosidase enzyme may come from various sources; however, in all cases, the β-glucosidase enzyme can hydrolyze cellobiose to glucose. The β-glucosidase enzyme may be a Family 1 or Family 3 glycoside hydrolase, although other family members may be used. In a preferred embodiment, the β-glucosidase enzyme is the Bgl1 protein from *Trichoderma reesei*. It is also contemplated that the β-glucosidase enzyme may be modified to include a cellulose binding domain, thereby allowing this enzyme to bind to cellulose.

In addition to CBH, EG and beta-glucosidase, there are several accessory enzymes that aid in the enzymatic digestion of cellulose (see co-owned WO 2009/026722 (Scott), which is incorporated herein by reference and Harris et al., 2010, Biochemistry, 49:3305-3316). These include EGIV, also known as glycoside hydrolase 61, swollenin, expansin, lucinen and cellulose-induced protein (Cip). Glucose can be enzymatically converted to the dimers gentiobiose, sophorose, laminaribiose and others by beta-glucosidase via transglycosylation reactions.

An appropriate cellulase dosage can be about 1.0 to about 40.0 Filter Paper Units (FPU or IU) per gram of cellulose, or any amount therebetween. The FPU is a standard measurement familiar to those skilled in the art and is defined and measured according to Ghose (Pure and Appl. Chem., 1987, 59:257-268; which is incorporated herein by reference). A preferred cellulase dosage is about 10 to 20 FPU per gram cellulose.

Cellulase enzymes can be added to the aqueous feedstock slurry prior to or during its introduction in the unmixed hydrolysis reactor or to the unmixed hydrolysis reactor itself. Examples of methods for adding enzyme include direct injection, which can involve the use of mixing tees; static or non-rotary mixing; or powered, in-line mixing, which can employ in-line rotary devices or in-line shredders. Alternatively, the enzymes may be added directly to the hydrolysis reactor, although the addition of enzymes prior to the introduction of the pretreated feedstock into the hydrolysis reactor is preferred for optimal mixing dispersion of the enzyme into the slurry. The enzymes may be handled in an aqueous solution or as a powder or granulate.

The enzymatic hydrolysis in the unmixed reactor produces soluble sugars, including glucose oligomers, dimers and/or glucose. The enzyme β-glucosidase can be omitted from the enzyme mixture, although it is preferred to include it during the hydrolysis as the glucose yield is significantly lowered in its absence.

The enzymatic hydrolysis is generally conducted at a pH between about 4.0 and 6.0 as this is within the optimal pH range of most cellulases. When the pH of the pretreated cellulosic feedstock is acidic, its pH will typically be increased with alkali to about pH 4.0 to about 6.0 prior to enzymatic hydrolysis, or more typically between about 4.5 and about 5.5. However, cellulases with pH optima at more acidic and more alkaline pH values are known.

The pH of the pretreated cellulosic feedstock may be adjusted with ammonia, ammonium hydroxide, potassium hydroxide, sodium hydroxide, potassium carbonate, potassium bicarbonate, sodium carbonate, sodium bicarbonate, calcium carbonate or lime, although pH adjustment is not limited to these chemicals. The alkali may be added as a solid, as a water solution or as a slurry. For example, the ammonia may be added as a gas or as ammonium hydroxide.

The alkali can be added to the pretreated feedstock after it is cooled, before cooling, or at points both before and after cooling. The point of alkali addition can coincide with the cellulase enzyme addition, or the addition point can be upstream or downstream of the location of the enzyme addition. If the enzyme is added upstream of the alkali addition point, the contact time of the enzyme at the lower pH of the pretreated feedstock would typically be minimized to avoid enzyme inactivation. Without being limiting, it is preferred that alkali is added prior to enzyme addition or simultaneously therewith.

The alkali may be added in-line to the pretreated feedstock, such as to an in-line mixer, to a pump downstream of pretreatment or directly to the unmixed reactor. A pump that comprises chemical injection ports, and that promotes mixing, such as medium consistency pump, can be employed to disperse alkali and enzyme simultaneously. Without being limiting, an in-line mixing device could be employed to add alkali and enzyme separately.

The temperature of the slurry is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. However, the temperature of the slurry may be higher for thermophilic cellulase enzymes. It should be understood that the temperature may not be constant throughout the reactor. For the purpose of the present specification, the temperature range is that of the majority of the reactor contents.

In order to maintain the desired hydrolysis temperature, the hydrolysis reactors may be jacketed with steam, hot water, or other heat sources. Moreover the reactors may be insulated to retain heat.

The hydraulic residence time in the unmixed reactor may be between 0.5 and 36 hours, between 4 and 24 hours or between 6 and 12 hours. The upper limit of this range is generally limited by flow instability.

The enzymatically treated feedstock resulting from the unmixed hydrolysis may resemble a plug of material, or the consistency may be such that it resembles an aqueous slurry. As used herein, the term "feedstock slurry" refers to either a pretreated feedstock that resembles an aqueous slurry or a mixture of partially hydrolyzed cellulose that resembles a plug of material.

In some embodiments, the enzymatic hydrolysis and fermentation are conducted in separate vessels so that each biological reaction can occur at its respective optimal temperature. However, the hydrolysis may be conducted simultaneously with fermentation in a simultaneous saccharification and fermentation. SSF is typically carried out at temperatures of 35-38° C., which is a compromise between the 50° C. optimum for cellulase and the 28° C. optimum for yeast.

Mixed Hydrolysis

According to some embodiments, the cellulosic feedstock slurry from the unmixed hydrolysis is subsequently fed to one or more hydrolysis reactors that hydrolyze the feedstock with mixing, as described hereinafter. In the unmixed reactor or reactor system, the enzymatic hydrolysis of the cellulose reduces the viscosity of the pretreated cellulosic feedstock. Advantageously, by reducing the viscosity of the pretreated feedstock by enzymatic hydrolysis, the power requirements associated with mixing are reduced during hydrolysis of the mixture of partially hydrolyzed cellulose in the subsequent mixed hydrolysis reactor(s).

It should be understood that viscosity measurements are dependent on the characteristics of the fluid being measured. For the purposes of this specification, the term "viscosity" is used in the qualitative sense to denote thick or thin slurries.

According to one embodiment of the invention, after completion of the unmixed hydrolysis, the percent conversion of the cellulose in the mixture of partially hydrolyzed cellulose is between about 10 wt % and about 70 wt %, or between about 15 wt % and about 65 wt %, or between about 10 wt % and about 50 wt %, or between 10 wt % and about 40 wt %, or any value therebetween. The percent hydrolysis of the cellulose in this mixture is measured according to the method of Example 2 and is measured at the outlet of the unmixed hydrolysis reactor or, if a system of unmixed hydrolysis reactors is employed, at the outlet of the last reactor in the system.

Various exemplary configurations of unmixed and mixed reactors in parallel, series and combinations thereof that can be employed in accordance with the invention are shown in U.S. Pat. No. 8,709,770, which is incorporated herein by reference. Mixing in the mixed hydrolysis reactor(s) may be achieved by any conventional means, including mechanical mixers such as top-mounted, side-mounted, or bottom-mounted impellers, agitators or eductors; rapid movement of liquid slurry streams pumped into or through the vessel; and/or introducing or generating gases or vapours in the vessel. A particularly suitable mixed hydrolysis reactor is a continuous stirred-tank reactor (CSTR reactor).

Similar to the unmixed hydrolysis, the enzymatic hydrolysis in the mixed hydrolysis is generally conducted at a pH between about 4.0 and 6.0 as this is within the optimal pH range of most cellulases. However, cellulases with pH optima at more acidic and more alkaline pH values are known.

The temperature of the slurry during the mixed hydrolysis is adjusted so that it is within the optimum range for the activity of the cellulase enzymes. Generally, a temperature of about 45° C. to about 70° C., or about 45° C. to about 65° C., or any temperature therebetween, is suitable for most cellulase enzymes. However, the temperature of the slurry may be higher for thermophilic cellulase enzymes.

The mixed hydrolysis reactor(s) may be subjected to light agitation, typically with a maximum power input of up to 0.8 hp/1000 gallons, or may receive heavy agitation of up to 20 hp/1000 gallons.

Optionally, additional cellulase enzyme can be added during the mixed hydrolysis.

When the hydrolysis is carried out in a mixed hydrolysis system that includes multiple mixed hydrolysis reactors, the number of mixed hydrolysis reactors in the system depends on the cost of the reactors, the volume of the aqueous slurry, and other factors. For a commercial-scale plant, the typical number of hydrolysis reactors may be for example, 3 to 12. Preferably, the mixed enzymatic hydrolysis is a continuous process, with continuous feeding of pretreated cellulosic feedstock and withdrawal of the glucose. However, it should be understood that batch and fed-batch processes are also included within the scope of the present invention.

In order to maintain the desired hydrolysis temperature, the contents of the hydrolysis reactor(s) are optionally heated or cooled. Heating or cooling may be carried out with heating or cooling jackets or by heat exchange with re-circulated slurry. The heating or cooling fluid used in the heat exchanger or in the jacket may include steam, hot water, cold water, glycol or brine. It should be understood that the temperature of the reactor contents during the mixed hydrolysis could be maintained within a desired range without any heating or cooling of the reactor contents.

Other design parameters of the mixed hydrolysis system may be adjusted as required. For example, the volume of a mixed hydrolysis reactor in a cellulase hydrolysis system can range from about 100,000 L to about 20,000,000 L, or any volume therebetween, for example, between 200,000 and 5,000,000 L, or any amount therebetween. The total residence time of the slurry in a hydrolysis system may be between about 12 hours to about 200 hours, or any amount therebetween.

After the mixed hydrolysis is complete, the product is glucose and any unreacted cellulose. Insoluble solids present in the resulting stream, including lignin, may be removed using conventional solid-liquid separation techniques prior to any further processing. However, it may be desirable to carry forward both the solids and liquids in the sugar stream for further processing.

According to one embodiment of the invention, between about 75% and about 100% (w/w) of the cellulose in the pretreated feedstock slurry is converted to glucose and/or cellobiose at the completion of the mixed hydrolysis, or between about 85% and about 95%, or any range therebetween. This includes ranges having numerical limits of 75, 80, 85, 90, 95 or 100%. Determination of the cellulose conversion is set forth in Example 2.

Fermentation

Fermentation of sugar resulting from the hydrolysis may produce one or more of the fermentation products selected from an alcohol, a sugar alcohol, an organic acid and a combination thereof (see also Feng et al., American Chemical Society, Jul. 11, 2011 In Sustainable Production of Fuels, Chemicals, and Fibers from Forest Biomass; Zhu, J., et al.; ACS Symposium Series; American Chemical Society: Washington, D.C., 2011).

The fermentation is typically conducted at a pH between about 4.0 and about 6.0, or between about 4.5 and about 6.0. To attain the foregoing pH range for fermentation, it may be necessary to add alkali to the stream comprising glucose.

In one embodiment, the fermentation product is an alcohol, such as ethanol or butanol. For ethanol production, the fermentation is typically carried out with a *Saccharomyces* spp. yeast. Glucose and any other hexoses present in the sugar stream may be fermented to ethanol by wild-type *Saccharomyces cerevisiae*, although genetically modified yeasts may be employed as well, as discussed below. The ethanol may then be distilled to obtain a concentrated ethanol solution. Butanol may be produced from glucose by a microorganism such as *Clostridium acetobutylicum* and then concentrated by distillation.

Xylose and arabinose that are derived from the hemicelluloses may also be fermented to ethanol by a yeast strain that naturally contains, or has been engineered to contain, the ability to ferment these sugars to ethanol. Examples of microbes that have been genetically modified to ferment xylose include recombinant *Saccharomyces* strains into which has been inserted either (a) the xylose reductase (XR) and xylitol dehydrogenase (XDH) genes from *Pichia stipitis* (see for example U.S. Pat. Nos. 5,789,210, 5,866,382, 6,582,944 and 7,527,927 and European Patent No. 450530) or (b) fungal or bacterial xylose isomerase (XI) gene (see for example U.S. Pat. Nos. 6,475,768 and 7,622,284). Examples of yeasts that have been genetically modified to ferment L-arabinose include, but are not limited to, recombinant *Saccharomyces* strains into which genes from either fungal (for example U.S. Pat. No. 7,527,951) or bacterial (for example WO 2008/041840) arabinose metabolic pathways have been inserted.

Organic acids that may be produced during the fermentation include lactic acid, citric acid, ascorbic acid, malic acid, succinic acid, pyruvic acid, hydroxypropanoic acid, itaconoic acid and acetic acid. In a non-limiting example, lactic acid is the fermentation product of interest. The most well-known industrial microorganisms for lactic acid production from glucose are species of the genera *Lactobacillus*, *Bacillus* and *Rhizopus*.

Moreover, xylose and other pentose sugars may be fermented to xylitol by yeast strains selected from the group consisting of *Candida*, *Pichia*, *Pachysolen*, *Hansenula*, *Debaryomyces*, *Kluyveromyces* and *Saccharomyces*. Bacteria are also known to produce xylitol, including *Corynebacterium* sp., *Enterobacter liquefaciens* and *Mycobacterium smegmatis*.

In practice, the fermentation is typically performed at or near the temperature and pH optimum of the fermentation microorganism. A typical temperature range for the fermentation of glucose to ethanol using *Saccharomyces cerevisiae* is between about 25° C. and about 35° C., although the temperature may be higher if the yeast is naturally or genetically modified to be thermostable. The dose of the fermentation microorganism will depend on other factors, such as the activity of the fermentation microorganism, the desired fermentation time, the volume of the reactor and other parameters. It should be appreciated that these parameters may be adjusted as desired by one of skill in the art to achieve optimal fermentation conditions.

The fermentation may also be supplemented with additional nutrients required for the growth of the fermentation microorganism. For example, yeast extract, specific amino acids, phosphate, nitrogen sources, salts, trace elements and vitamins may be added to the hydrolyzate slurry to support their growth.

The fermentation may be conducted in batch, continuous or fed-batch modes with or without agitation. Preferably, the fermentation reactors are agitated lightly with mechanical agitation. A typical, commercial-scale fermentation may be conducted using multiple reactors. The fermentation microorganisms may be recycled back to the fermentor or may be sent to distillation without recycle.

If ethanol or butanol is the fermentation product, the recovery is carried out by distillation, typically with further concentration, such as by molecular sieves or membrane extraction.

The fermentation broth that is sent to distillation is a dilute alcohol solution containing solids, including unconverted cellulose, and any components added during the fermentation to support growth of the microorganisms.

Microorganisms are potentially present during the distillation depending upon whether or not they are recycled during the fermentation. The broth is preferably degassed to remove carbon dioxide and then pumped through one or more distillation columns to separate the alcohol from the other components in the broth. The mode of operation of the distillation system depends on whether the alcohol has a lower or a higher boiling point than water. Most often, the alcohol has a lower boiling point than water, as is the case when ethanol is distilled.

In those embodiments where ethanol is concentrated, the column(s) in the distillation unit is preferably operated in a continuous mode, although it should be understood that batch processes are also encompassed by the present invention. Heat for the distillation process may be introduced at one or more points either by direct steam injection or indirectly via heat exchangers. The distillation unit may contain one or more separate beer and rectifying columns, in which case dilute beer is sent to the beer column where it is partially concentrated. From the beer column, the vapour goes to a rectification column for further purification. Alternatively, a distillation column is employed that comprises an integral enriching or rectification section.

After distillation, the water remaining may be removed from the vapour by a molecular sieve resin, by membrane extraction, or other methods known to those of skill in the art for concentration of ethanol beyond the 95% that is typically achieved by distillation. The vapour may then be condensed and denatured.

An aqueous stream(s) remaining after ethanol distillation and containing solids, referred to herein as "still bottoms", is withdrawn from the bottom of one or more of the column(s) of the distillation unit. This stream will contain inorganic salts, unfermented sugars and organic salts.

When the alcohol has a higher boiling point than water, such as butanol, the distillation is run to remove the water and other volatile compounds from the alcohol. The water vapor exits the top of the distillation column and is known as the "overhead stream".

The present invention will be further illustrated in the following examples. However, it is to be understood that these examples are for illustrative purposed only, and should not be used to limit the scope of the present invention in any manner.

EXAMPLES

Example 1: Determination of the Undissolved Solids Concentration in a Cellulosic Feedstock Slurry The determination of the undissolved solids (UDS) content is carried out as follows.

A fixed amount of slurry is dispensed into a plastic weigh dish and the slurry weight is recorded accurately using an analytical scale. A filter paper circle, appropriately sized for a Buchner funnel, is placed in an aluminum weighing tin and the combined weight of the tin and filter paper is recorded. After transferring the pre-weighed filter paper to the Buchner funnel, the pre-weighed slurry is passed through the filter paper to isolate the solids. Small volumes of de-ionized water are used to ensure that the solids are quantitatively transferred from the weigh dish to the Buchner funnel. The solids are then washed using excess deionized water, after which the washed sample and filter paper are transferred into the pre-weighed aluminum tin. Care should be taken to ensure the solids are quantitatively transferred. After drying the aluminum tin in a 105° C. oven overnight, the contents are weighed accurately and the UDS is quantified by determining, as a percent, the number of grams of dry solids per gram of slurry.

Example 2: Determination of the Degree of Conversion of Cellulose after Unmixed or Mixed Hydrolysis The degree of cellulose conversion is determined by measuring the initial cellulose, glucose and cellobiose concentrations and the concentrations of glucose and cellobiose after unmixed or mixed hydrolysis has taken place, and applying the following equations.

$$X = \left[\frac{(G - G_o) + 1.053(G_2 - G_{2o})}{G_{max}}\right]100$$

$$G_{max} = \frac{1.11 C_o \left[1.02 + 0.041\left(C_o + \frac{X_o}{1000}\right)\right]}{1 - C_o}$$

X=Cellulose conversion (%)
G=Glucose concentration (g/L)
Go=Initial glucose concentration (g/L)
$G_2$=Dimer concentration (g/L); includes primarily cellobiose, but also gentiobiose and other dimers
$G_{2o}$=Initial dimer concentration (g/L); includes primarily cellobiose, but also gentiobiose and other dimers
Gmax=Glucose concentration at 100% cellulose conversion (g/L)
Co=Initial cellulose concentration (%)
Xo=Xylose concentration (g/L)

Example 3: Residence Time Distribution of Slurry Flowing Through a Vertical Reactor Comprising an Inlet Dissipator Device This example demonstrates that the use of a slurry introduction device in a plug flow reactor comprising a vertical inlet pipe and a distributor plate can increase the residence time of a cellulosic feedstock slurry relative to a reactor without such device.

The feedstock used in this example was sugarcane bagasse. The sugarcane bagasse was subjected to particle size reduction and pretreated with sulfuric acid at elevated temperature. The reaction conditions for the pretreatment were as set forth in U.S. Pat. No. 7,754,457, which is incorporated herein by reference.

The residence time for the pretreated cellulosic feedstock slurry was studied in a vertical plug flow reactor. The cellulosic feedstock slurry was introduced at the top of the plug flow reactor and then traveled downwardly through the reactor to its outlet. The slurry introduction device used in this example is shown in FIG. 1B. The plug flow reactor had a length to diameter ratio of 2 and the volume was 220 L. The flow rate of the pretreated cellulosic feedstock slurry was between 25 and 30 L/min, so the expected mean residence time was 7.3 to 8.4 minutes.

With reference to FIG. 1B, the incoming cellulosic feedstock slurry was fed through inlet piping 4 and a disk-shaped distributor plate 16 was placed 8 inches below the outlet of the inlet piping 4 on the surface of the reactor contents 8. The distance of the drop from the proximate end of the inlet piping 4 to the surface of the slurry in the inlet region 6 of the plug flow reactor was 8 inches. In order to compare the effect of the residence time with and without a distributor plate, the residence time was also measured by introducing the pretreated cellulosic slurry via inlet piping 4 without a distributor plate placed below its outlet.

The residence time was quantified as a residence time distribution (RTD) with tracer studies, using iodide as the tracer. The iodide tracer was introduced to the inlet of the plug flow reactor and the time for it to travel down through the reactor and exit through the outlet was measured and quantified as a breakthrough time. The breakthrough time was then compared to a calculated expected mean residence time which assumed ideal plug flow. The residence time distribution was determined in this example for two different undissolved solids (UDS) concentrations; namely 12.8 and 11.6 wt %.

The ratio of the measured breakthrough time of the tracer versus the calculated expected mean residence time was used to quantitatively assess the effective volume of the reactor. A fast tracer breakthrough, as indicated by a lower than unity ratio between breakthrough time and expected mean residence time, evidences channeling and a stagnant volume in the plug flow reactor.

Figure 2:
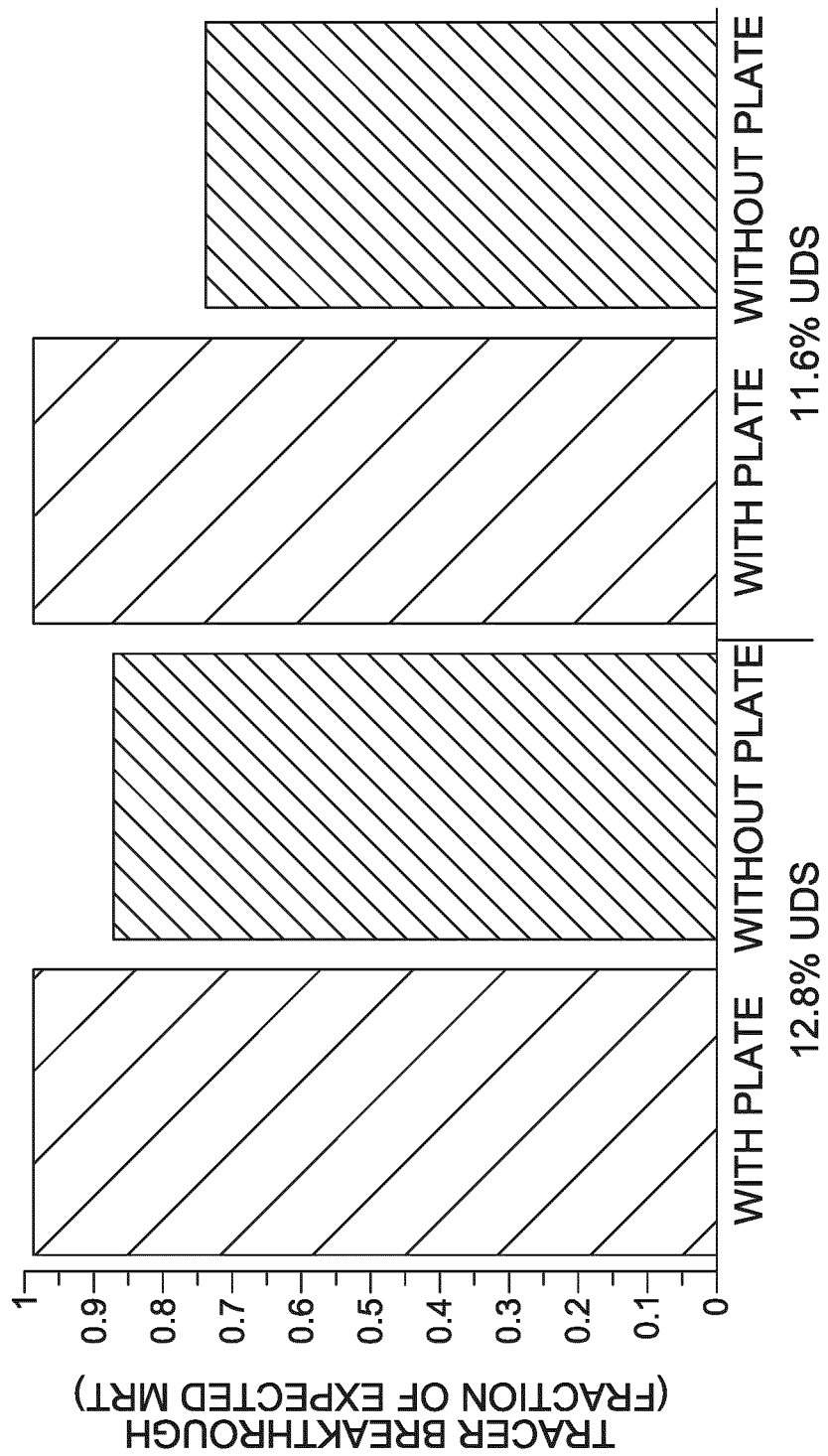
FIG. 2 shows the tracer breakthrough (KI) for pretreated cellulosic feedstock flowing downwardly through a plug flow hydrolysis reactor measured as a fraction of the expected mean residence time (fraction of expected MRT) with and without a slurry introduction device comprising a distributor plate at undissolved solids concentrations of 12.8 wt % and 11.6 wt %.

The data in FIG. 2 show the positive effect of the inlet feed distributor plate on the tracer breakthrough time. When the distributor plate is used to dissipate the axial momentum of the incoming feed, the tracer breakthrough time is closer to the expected mean residence time. The data in FIG. 2 thus predicts that the use of a slurry introduction device comprising a distributor plate would lead to higher reactor volume efficiency compared to without the provision of such a plate.

It should be understood that the foregoing examples are for illustrative purposes only and should not be construed to limit the current invention in any manner.

We claim:

1. A process for producing glucose from a cellulosic feedstock, said process comprising the steps of:
   (i) providing a pretreated cellulosic feedstock slurry having an undissolved solids content of between about 5 and about 40 wt % undissolved solids;
   (ii) conveying the pretreated cellulosic feedstock slurry to a continuous plug flow hydrolysis reactor;
   (iii) introducing the cellulosic feedstock slurry to an inlet region of the continuous plug flow hydrolysis reactor using a slurry introduction device that reduces axial momentum of the slurry at the surface of the reactor contents; and
   (iv) hydrolyzing said pretreated cellulosic feedstock slurry in the plug flow hydrolysis reactor by contacting the cellulosic feedstock with at least cellulase enzymes to produce glucose.

2. A process for producing glucose from a cellulosic feedstock, said process comprising the steps of:
   (i) providing a pretreated cellulosic feedstock slurry having an undissolved solids content of between about 5 and about 40 wt % undissolved solids;
   (ii) conveying the pretreated cellulosic feedstock slurry to a continuous plug flow hydrolysis reactor;
   (iii) introducing the cellulosic feedstock slurry to an inlet region of the continuous plug flow hydrolysis reactor using a slurry introduction device that reduces axial momentum of the slurry at the surface of the reactor contents; and
   (iv) hydrolyzing said pretreated cellulosic feedstock slurry in the plug flow hydrolysis reactor by contacting the cellulosic feedstock with at least cellulase enzymes to produce glucose,
   wherein the slurry introduction device comprises two or more feed ports that introduce slurry horizontally through a wall of said reactor adjacent to a top region of the reactor contents.

3. The process of claim 1, wherein the hydrolysis is carried out with beta-glucosidase.

4. The process of claim 1, wherein a partially hydrolyzed cellulosic feedstock from step (iv) is fed to a mixed hydrolysis reactor and further hydrolyzed therein.

5. The process of claim 1, wherein the portion of the cellulose hydrolyzed in the plug flow reactor is between about 10 wt % and about 100 wt %.

6. The process of claim 1, wherein the slurry introduction device further comprises:
   a) two or more feed ports that introduce slurry horizontally through a wall of said continuous plug flow hydrolysis reactor adjacent to a top region of the reactor contents;
   b) a feed port that terminates with a distributor plate disposed in an inlet region of the continuous plug flow hydrolysis reactor;
   c) a pipe and first and second disk-shaped distributor plates, said first and second disk-shaped distributor plates positioned one on top of the other with a gap therebetween such that pretreated cellulosic feedstock slurry fed through the pipe flows through the gap; or
   d) a pipe and a rotatable horizontal arm, said rotatable arm comprising first and second outlet ports.

7. The process of claim 1, wherein the slurry introduction device further comprises a distributor plate disposed in an inlet region of the continuous plug flow hydrolysis reactor.

8. The process of claim 1, wherein the slurry introduction device further comprises a pipe and first and second disk-shaped distributor plates, said first and second disk-shaped distributor plates positioned one on top of the other with a gap therebetween such that pretreated cellulosic feedstock slurry fed through the pipe flows through the gap.

9. The process of claim 1, wherein the slurry introduction device further comprises a pipe and a rotatable horizontal arm, said rotatable arm comprising first and second outlet ports.

10. The process of claim 1, wherein the slurry introduction device further comprises a dissipator device configured to disperse the slurry at an angle off-set from the direction of slurry flow.

11. The process of claim 1, wherein the slurry introduction device further comprises a distributor plate.

12. The process of claim 1, wherein the slurry introduction device further comprises an inverted cone.

13. The process of claim 1, wherein the slurry introduction device further comprises:

a) one or more feed ports that introduce slurry horizontally through a wall of said continuous plug flow hydrolysis reactor adjacent to a top region of the reactor contents;
b) a feed port that terminates with a distributor plate disposed in an inlet region of the continuous plug flow hydrolysis reactor;
c) a pipe and first and second disk-shaped distributor plates, said first and second disk-shaped distributor plates positioned one on top of the other with a gap therebetween such that pretreated cellulosic feedstock slurry fed through the pipe flows through the gap;
d) a pipe and a rotatable horizontal arm, said rotatable arm comprising first and second outlet ports; or
e) an inverted cone.

* * * * *